(12) United States Patent
Schedler et al.

(10) Patent No.: US 6,227,852 B1
(45) Date of Patent: May 8, 2001

(54) DENTAL IMPRESSION CURETTE

(76) Inventors: Markus Schedler, Höhstrasse 13a, D-67714 Waldfischbach (DE); Hubertus Platt, Hansaalle 109, D-60320 Frankfurt (DE)

(*) Notice: Subject to any disclaimer, the term of this patent is extended or adjusted under 35 U.S.C. 154(b) by 0 days.

(21) Appl. No.: 09/214,873

(22) PCT Filed: Jul. 16, 1997

(86) PCT No.: PCT/EP97/03800
§ 371 Date: Aug. 9, 1999
§ 102(e) Date: Aug. 9, 1999

(87) PCT Pub. No.: WO98/02111
PCT Pub. Date: Jan. 22, 1998

(30) Foreign Application Priority Data

Jul. 16, 1996 (DE) .............................................. 196 28 682

(51) Int. Cl.[7] ...................................................... A61C 9/00
(52) U.S. Cl. .................................................. 433/37; 433/45
(58) Field of Search .................................. 433/37, 38, 41, 433/42, 45, 47

*Primary Examiner*—Nicholas D. Lucchesi
(74) *Attorney, Agent, or Firm*—St. Onge Steward Johnson & Reen LLC (57) ABSTRACT

The invention concerns a dental mold tray for producing tooth casts by means of a hardenable mold mass, with a molding shell (10) adapted to the shape of the human upper or lower jaw, for the reception of the mold mass, so that the molding shell (10) can be separated into at least two parts for the non-destructive reception of the hardened mold mass bearing the tooth impression. The mold tray includes a saliva drainage device (64), which extends along the inside edge area turned toward the tongue and/or along the outside edge turned toward the cheek or lip and is removably connected with the outer and/or inner side wall (22, 16). For improved adaptation, an elastic and/or moldable insulation and balancing element (48) is provided, which during the casting process produces a fluid contact between the molding shell (10) and the membrane or gum.

42 Claims, 5 Drawing Sheets

DENTAL IMPRESSION CURETTE

DESCRIPTION OF THE INVENTION

The invention concerns a dental mold tray for producing tooth impressions by means of a hardenable molding material, with a molding shell adapted to the shape of the human upper or lower jaw for the formation of the mold mass.

Rigid mold trays are well known for the production of tooth impressions, in a process whereby an impression is first made of the teeth in the patient's mouth using molding material. The resulting negative form is then filled in with plaster or similar material. Next, the molding tray is destroyed in order to extract the plaster model from the mold mass in a condition that is as undamaged as possible.

For this purpose, Patent DE 17 66 510 proposes a mold tray made of plastic with the border area of the molding shell formed in such a way that the hardened impression mass can be removed from the mold tray by breaking off parts of the tray in fragments. As a result, however, this kind of mold tray can be used only once. In addition, it is necessary to have a series of such mold trays on hand in order to have one usable tray available that matches the anatomical characteristics of the individual patient's jaw.

The aim of this invention therefore was to come up with a reusable, universal dental mold tray which permits the production of very exact tooth impressions in a simple manner by means of a hardenable mold mass.

To fulfill this aim, the invention developed an object having the characteristics stated in Patent Claim 1; the subsidiary claims include at least appropriate realizations and further adaptations. In keeping with the invention, the molding shell can be separated into at least two components in order to permit the removal of the mold mass with its tooth impression without destruction.

The mold tray according to this invention allows a simple, non-destructive removal of the hardened mold mass after the impression is made. Any breakage or damage of the tooth impression is thus effectively avoided and there is no need for expensive further processing or reconstruction in the dental laboratory. In addition, the individual parts of the invention's mold tray are easy to clean.

In accordance with the basic concept of the invention, the molding shell consists of a base plate adapted to the gum or to the tongue area, and a roughly U-shaped external side wall long its edge which surrounds the respective tooth row with its at least partially arched shape. The base plate and the outer side wall are thus connected but can be detached from one another. To ensure the non-destructive removal of the hardened mold mass, thus only the outer side wall must be removed from the base plate and from the hardened mold mass. This definitely alleviates the removal of the completed tooth mold from the mold tray.

Another advantage is that the base plate slopes upward in the direction of the gums for the upper jaw impression. As a result of this arrangement, swallowing is alleviated during the molding process and any possibility of gagging is prevented. Because of the reduced distance between the base plate and the gums or the teeth, a lesser amount of molding material is required. This increases the exactitude of the mold on the one hand, and reduces the materials costs on the other.

For taking molds of the lower jaw, it is advisable to equip the base plate with a roughly U-shaped tongue opening. The edge area of this tongue opening is bordered with an inner side wall, which runs at least partially behind the respective tooth row. By means of the inner side wall, the tongue or the mucous membrane is kept effectively separated from the mold mass and the molding shell can be restricted to a minimal volume. This also allows for materials economies and increases the exactness of the impression.

To ensure ease in inserting or removing the mold tray in taking an impression, the base plate can be equipped with a handle extending outward from the tooth row out of the mouth.

In accordance with another basic concept in the invention, the outer side wall and/or the inner side wall is connected to the base plate and segmented so as to allow removal.

The side wall thus can be easily separated from the base plate; first, the side wall can be rotated with respect to the base plate and then it can be totally removed. This ensures non-destructive removal of the hardened molding material.

To avoid any undesired overflow of the mold mass between the base plate and outer and/or inner side wall, especially during filling of the mold tray with the mold mass or at the start of the casting when the mold mass has not yet hardened, the base plate is equipped with a trough to engage the inner or outer side wall. A useful feature is the presence of a washer or sealing device between the base plate and the inner or outer side wall.

To ensure a secure link between the base plate and the inner and/or outer side wall during the casting process, the inner and/or outer side wall can be connected with the base plate by means of a separable linking device that can take the form of a catch, clamp, bolt, or similar item.

As a further advantage, the outer and/or inner side wall includes an extension which comes into play when the base plate and the respective side wall are connected with the handle of the base plate, and here the handle and the respective extension are connected by means of a clamp ring, a U-shaped clamp device that moves in a sidewise manner, a catch or bolt connection or similar removable connecting device. An arrangement of this kind results in a secure connection between the base plate and the respective side walls, and here the construction units can be easily separated from one another in a simple manner.

In keeping with an additional proposal, the inner and/or outer side wall is arranged to adapt flexibly to the form and/or size of the base plate and of the patient's jaw area.

In this manner, different kinds of base plates, depending on the anatomical characteristics of the patient, can be supplemented with standardized side walls. The side walls to be used can also be of various forms, and in particular may have varying heights. This results in a series of possible combinations, so that it is not necessary to have a great number of different mold clamps in inventory in order to produce an exact impression. Consequently, the mold clamp is adaptable to specific patients with exactitude while costs can be appreciably reduced.

According to another basic idea of the invention, at least one securing stud is installed in the molding shell between the base plate and the outer side wall or between the inner and outer side walls. When a cast is being made, especially with flexible side walls, misshaping of the molding shell by intrusive forces through pressure against molding material from the teeth can be avoided and thus a more exact tooth impression can be realized.

At least one stud can be glued in between the base plate and outer side wall or between the inner and outer side walls, or secured in similar fashion. If necessary the stud or studs can be removed or broken out, something that may be required in particular during removal of the hardened molding material.

In accordance with an additional idea of the invention, at least one stud between the base plate and outer side wall or between the inner and outer side walls can be installed in removable state in the corresponding casting devices either as a plug-in, a clamp, or other means. In this way, at least one stud can be removed without any damage to the mold tray when the hardened mold mass is taken out. Thus, the mold tray can be installed repeatedly either with or without the stud.

In another basic concept of the invention, the edge area of the inner and/or outer side wall and of the base plate that comes in contact with the membrane or the gum during casting has an elastic and/or re-shapeable washer or balance element for improved adaptation. It is therefore possible to bring the entire edge area of the molding shell into exactly formed, secure contact with the membrane or gum. As a result, before casting, the unfilled mold tray can be adjusted to the corresponding jaw area of the patient or temporarily inserted for testing. Only after this step is the mold tray filled with the molding material. Consequently, thanks to the precisely adjusted shaping of the molding shell, only a limited amount of molding material is required.

Especially good airtightness and simultaneously form-fast adjustment of the edge area to the membrane or gum is offered by thermoplast, self-hardening silicon, or non-hardening plastic. Obviously, every other reshapeable and/or hardenable material is also suitable for the airtightness or adjustment element.

The airtightness and adjustment element can be installed in a molding device on the inner and outer side wall and the base plate. At the same time the molding device can, in particular, also include a channel running around the edge area of the inner and outer side wall and of the base plate.

In another basic concept of the invention, the base plate and/or the inner and/or outer side wall can have at least one drainage opening for producing a partial vacuum between the membrane or gum and the molding shell. This enables it to be connected with a drainage link for a pumping mechanism by way of at least one drainage channel in the base plate or in the inner or outer side wall. The pump installation makes it possible to create a vacuum between the molding shell and the membrane or gum, so that the mold tray is in a better position when it is not filled with mold mass.

It is especially advantageous if the drainage link for the pumping device is on the handle itself.

In order now for the mold mass to be placed in the molding shell, the base plate and/or the inner and/or outer side wall has at least one injection opening, which can be connected by means of an injection channel in the base plate and/or outer side wall with a link for a mold mass injection device.

By means of these devices, it is easily possible to inject a viscous, hardenable mold mass from the area of the molars into the mold tray which is already in the mold position and unfilled. The high pressure, often unpleasant for the patient, which must be used by the dentist in order to press an already filled mold tray for the impression against the tooth row, is not necessary. An additional advantage is the fact that the mold mass has high viscosity at the time of injecting and thus can penetrate well into the intervals between teeth and in the recesses in the tooth material. It is thus much easier to obtain extremely exact tooth impressions.

In making a cast it is often disturbing that the tongue or cheek area comes into direct contact with the mold tray. In order to avoid this immediate contact, the molding shell includes a soft-area protection for covering the tongue and/or cheek area or keeping it at a distance. Thus, the base plate and/or the inner side wall can be equipped with a tongue shield and the outer side wall can have a cheek protector.

In addition, the natural formation of saliva in the oral cavity during casting is disturbing and can affect the quality of the mold results.

In a further concept of the invention, therefore, the inner side wall and/or outer side wall includes a saliva drainage device for the casting process, located on the inner wall area toward the tongue and/or on the outer wall toward the cheek or lip. In this way, saliva formed during casting can be removed easily.

The saliva drainage device can include a saliva drainage channel with numerous drainage openings. It is possible for a connection to the saliva drainage device for the saliva drainage pump to be situated on the handle. This makes it easier to attach such a drainage pump.

As an advantageous refinement, the saliva drainage device can be detachable from the molding shell. The saliva drainage device can thus be hinged so as to be detachable from the molding shell. Because the molding shell can be installed together with, or else separate from, the saliva drainage device, a whole series of combinations and applications are possible.

Thus, for instance, the saliva drainage device can be installed on teeth during the preparation phase, so that the tooth is kept dry and the cheek and tongue are kept away, without the presence of an assistant being required.

To create an insulated connection between the saliva drainage device and the molding shell, the saliva drainage device includes a trough to hold the edge portion of the molding shell. The trough can include an undercutting and the edge portion of the molding shell can have a notch projection, in such a way the notch projection can mesh with the undercutting, in order to make a detachable link between the saliva drainage device and the molding shell. In this connection it is especially advantageous that a fluid-proof installation is in place between the saliva drainage device and the molding shell.

It is also conceivable, however, that the saliva drainage device can be affixed to the molding shell by means of a notch, clamp, bolt, or similar detachable connection device.

To ensure an especially close adjustment of the saliva drainage device to the patient's jaw area, one possibility is for the saliva drainage device to be formed of flexible material so that it can be adapted to the shape and/or size of the molding shell and to the patient's jaw area. An alternative possibility is that the insulation and equilibrium element can be arranged along the saliva drainage device. In this case the fixture for holding the insulation and equilibrium element is included on the saliva drainage device. In addition, the saliva drainage device can include the soft-area protection for distancing or covering the tongue and cheek area.

To enable the molding shell to be held in the casting position while the impression is taken, a securing device is called for. In the case of a molding shell for a lower jaw casting, this can take the form of a chin clamp attachable on the base plate and/or the outer side wall. The mold tray for an upper jaw casting, on the other hand, can include a securing strap attaching to the base plate and/or outer side wall and extending across the top of the patient's head.

The mold tray of this invention ensures that an exact tooth impression is made in a simple manner and can be applied in diverse ways and also be reused.

The invention is considered in greater detail below in a series of demonstrations and with the help of illustrations.

Figure 1:
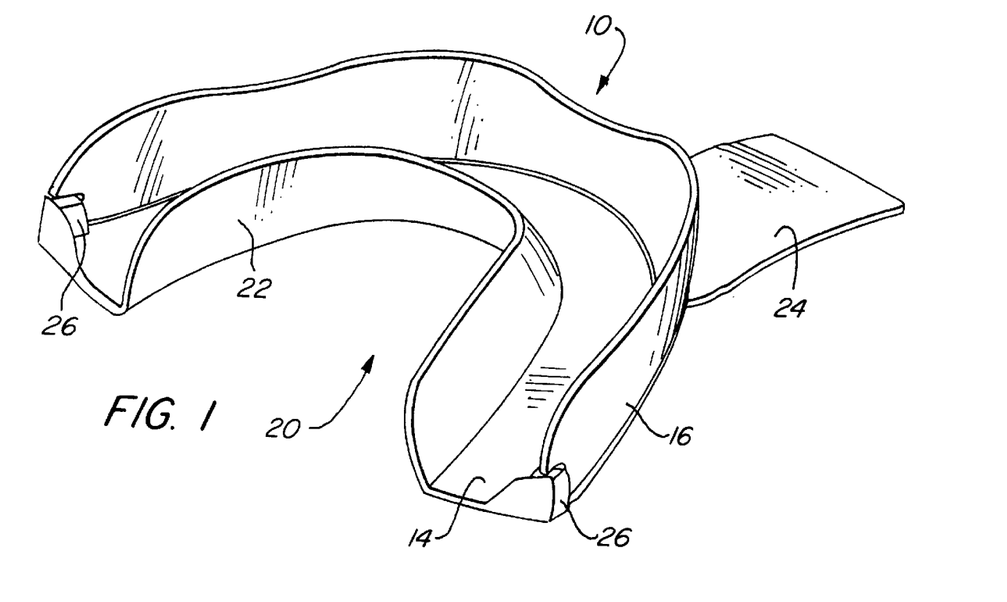
FIG. 1 Demonstration of the invention's mold tray for lower jaw molds in a schematic-perspective view.

FIG. 1 shows a mold tray of fiberglass-reinforced plastic for casting of the lower jaw. The illustrated mold tray may also be made of steel or some other metal, of ceramic or plastic, or of a combination of these materials. The mold tray 10, which surrounds the teeth of the lower jaw during casting, is filled for casting with a hardenable mold mass (not shown). The mold mass can be self-hardening or light-hardening. The mold tray shown in FIG. 1 consists basically of a base plate 14, which includes a roughly U-shaped tongue opening. The edge portion of the tongue opening 20 is bordered with an inner side wall 22, which during casting runs along the back side of the tooth row. Along the front of the tooth row there is a roughly U-shaped outer side wall 16 in the edge portion of the base plate 14. This outer wall surrounds the corresponding tooth row in a gently curved shape. The outer side wall 16 is segmented so as to be detachable from the base plate 14. For this purpose a segmented connection device 26 is installed in the area of the molars between the base plate 14 and the outer side wall 16.

In order to be able to insert the mold tray easily into the mouth for casting, a handle 24 is formed on the base plate 14 extending outward from the tooth row from the mouth. The handle 24 also serves to raise the mold tray with its hardened molding material bearing the tooth impression, and to lift it from the lower jaw and to remove it from the mouth.

To allow the hardened mold mass to be removed from the molding shell 10 without destruction, the outer side wall 16 opposite the base plate 14 can be rotated by means of the segmented connecting device 26. In addition the segmented connecting device 26 allows for a complete removal of the outer side wall 16 from the base plate 14.

Figure 2:
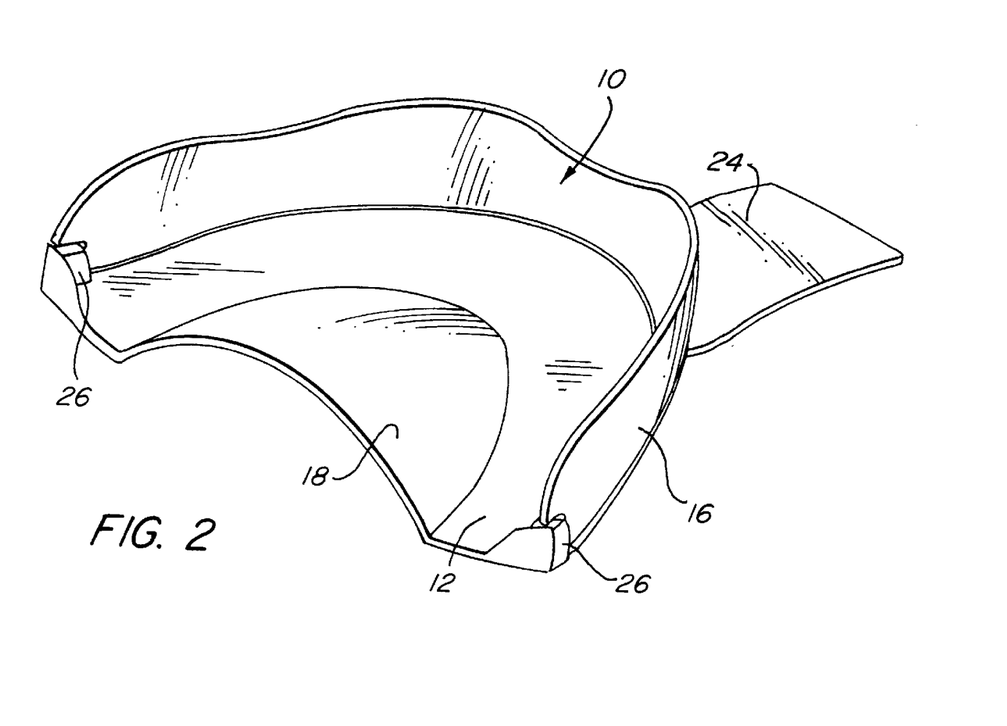
FIG. 2 Demonstration of the invention's mold tray for upper jaw molds in schematic-perspective view.

FIG. 2 shows a mold tray for casts on the lower jaw. The mold tray also has a base plate 12 and an outer side wall 16 connected with the base plate by means of a segmented connecting device 26 in the molar region and detachable from it. The difference between the mold tray shown in FIG. 2 for the upper jaw molding and the mold tray shown in FIG. 1 for casting the lower jaw, consists in the form of the base plate 12. Base plate 12 has a vaulted top 18 rising in the direction of the gums, which top protects the soft gums during casting. Because of the anatomical characteristics of the upper jaw, such a shape for the base plate 12 with a gum vault 18 is preferable to a gum opening in the gum area. That type of configuration is, however, possible.

FIG. 3 shows again a mold tray for casting on the lower jaw. Contrary to the mold tray shown in FIG. 1, the inner side wall 22 is also segmented and detachable from the base plate 14. A segmented connecting device 27 is installed for this purpose in the molar region inside the tooth row. Thus, by rotating both the outer side wall 16 and the inner side wall 22 with respect to the base plate, the hardened molding material can be removed in an extremely simple manner and undamaged.

Figure 3:
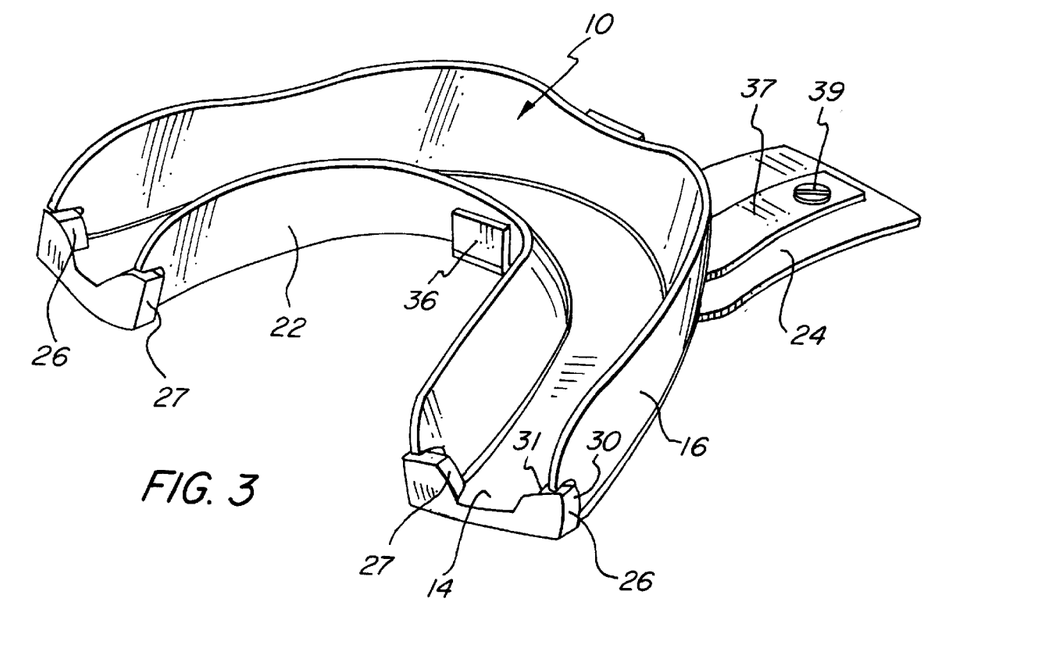
FIG. 3 An addition demonstration of the invention's mold tray for a lower jaw mold in schematic-perspective view.

As can further be seen from FIG. 3, both on the outer and inner side wall there are extensions (37 and 36 respectively). Extension 37 of the outer side wall 16 is roughly L-shaped and is connected from the outer side wall 16 and the base plate 14 with the handle 24. Extension 36 of the inner side wall 22 is also roughly L-shaped and is connected with the handle 24 on the side turned toward extension 37 in such a way that by means of a screw connection 39 both extensions 37 and 36 are detachable from the handle. Extensions 37 and 36 are of a stable material such as stainless steel and ensure safe adhesion between the outer or inner side wall (16 or 22, respectively) with the base plate 14.

Figure 4:
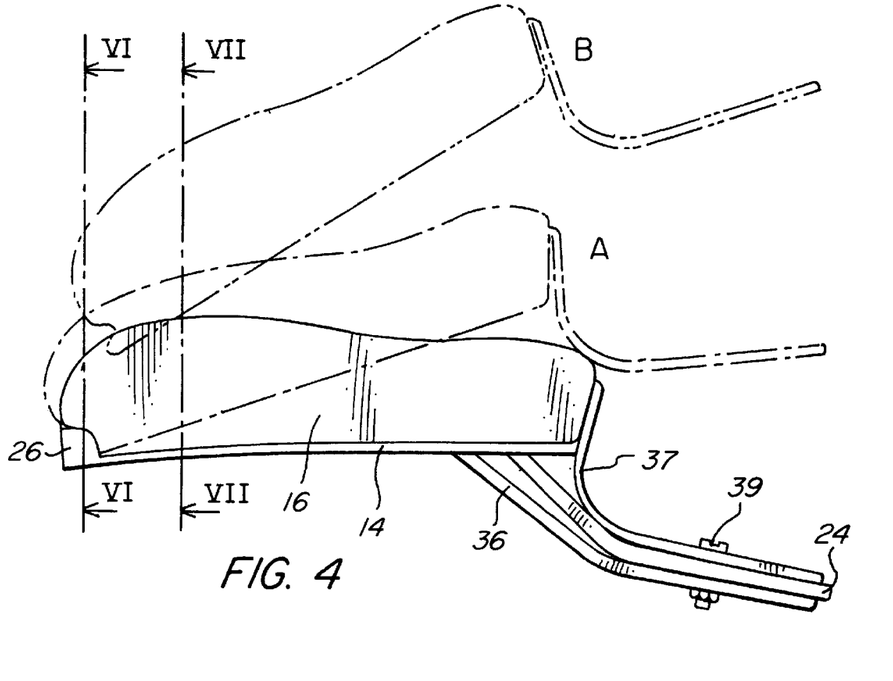
FIG. 4 A schematic side view of the invention's mold tray according to FIG. 3.

FIG. 4 shows the mold tray of FIG. 3 in a schematic lateral view. In the firmly drawn lines in the lower area of the illustration, the mold tray is shown in "closed" position, in which both the inner side wall 22 and the outer side wall 16 are attached to the handle 24 by way of extensions 36 and 37 by means of a bolt 39 with nut. In position A, indicated with broken lines, the outer side wall 16 is shown rotated away from the base plate 14 so that the end of outer side wall 16 lying in the molar region is held by the segmented connecting device 26 and moves around this device. In position B, drawn with alternating dots and lines, the outer side wall 16 is shown completely detached from the base plate 14 or the segmented connecting device 26.

The outer side wall 16, starting from position B, can be returned in simple manner into the segmented connecting device 26, so that it is again in position A. Merely by rotating the outer side wall 16 from position A into the "closed" position and by securing extension 37 to the handle 24, the mold tray in the illustration is ready for the next molding process.

Figure 5:
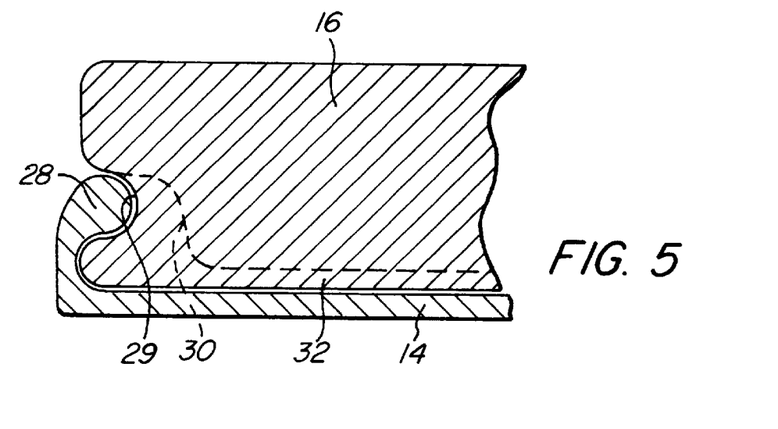
FIG. 5 A schematic partial longitudinal section of the segmented connector device for the outer side wall of the invention's mold tray according to FIG. 3.
Figures 6, 7:
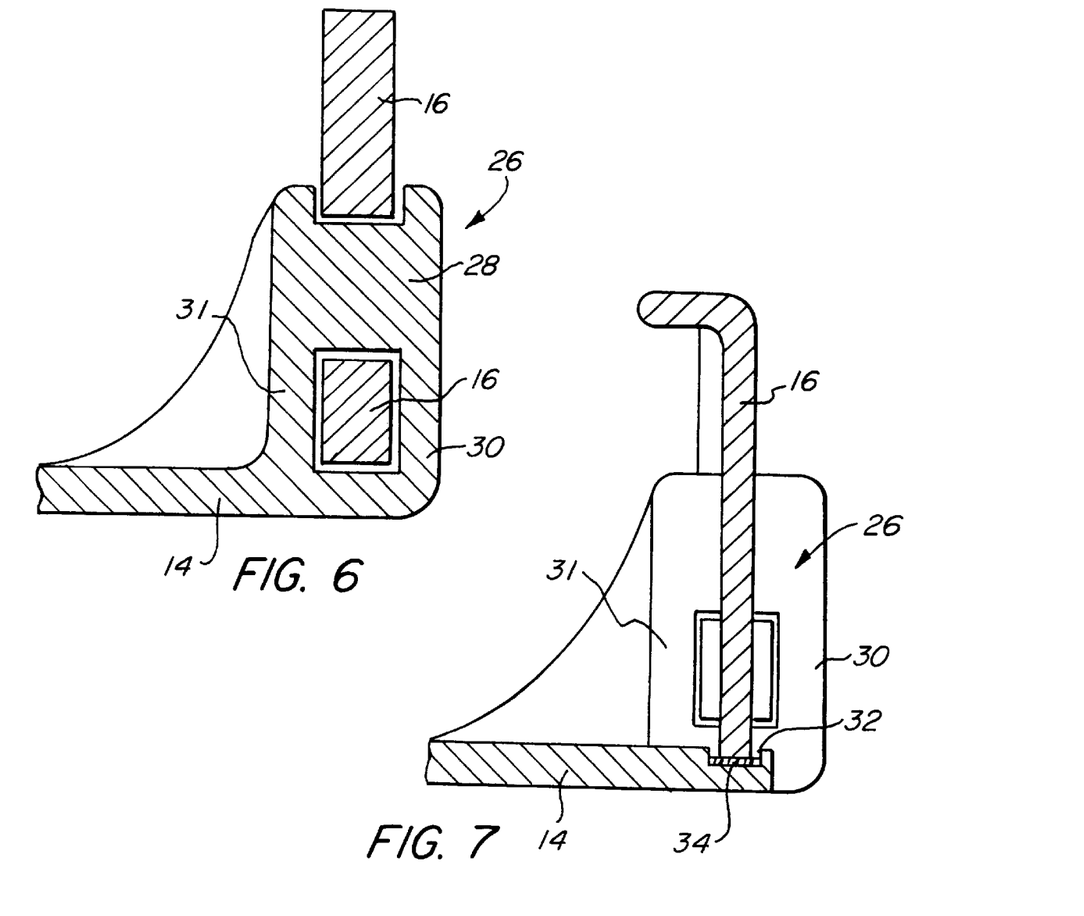
FIG. 6 A schematic partial cross-section of the mold tray according to FIG. 4 in the section along the line VI—VI in FIG. 4.
FIG. 7 A schematic partial cross-section of the mold tray according to FIG. 4 in the section along the line VII—VII in FIG. 4.

FIG. 5 shows the articulated connecting device 26 in a longitudinal section. FIG. 6 presents the mold tray, according to FIG. 4, in a cross section along the line VI—VI of FIG. 4, while FIG. 7 shows it in cross-section along the line VII—VII of FIG. 4. The following explanations for the segmented connecting device 26 of the outer side wall 16 also apply basically to the articulated connecting device 27 of the inner side wall 22.

The articulated connecting device 26 is described with reference to FIGS. 5 to 7. On the back end of the outer side wall 16, in the molar region, there is an opening 29 that runs in roughly horizontal direction.

On the base plate 14 in the molar region there is a stud 28 which supports the rear end of the outer side wall 16 and which also is positioned horizontally, that is, roughly parallel to the base plate 14. When the outer side wall 16 (compare position A in FIG. 4) is installed, the stud 28 engages with the opening 29 of the outer side wall 16. Both the opening 29 and the stud 28 are rounded in shape at their points of contact, so that the outer side wall 16 can be easily rotated around the stud 28 as the axis of rotation. The meshing of the stud 28 with the opening 29 effectively prevents a vertical motion of the outer side wall from the base plate 14.

If the stud 28 and/or the opening 29 in the outer side wall 16 has an elliptical shape (not shown), it is possible to exert pressure on the outer side wall 16 vertically in the direction of the base plate 14 by moving the outer side wall from position A as shown in FIG. 1 to the "closed" position. In this manner it is possible to obtain a well-insulated contact and a stable connection between the outer side wall 16 and the base plate 14 in the molar region.

To prevent that the end of the outer side wall in the molar region might slide in the direction perpendicular to the tooth row, on both sides of the stud 28 there is a limiting wall 31 and 30, one part of which is placed inside the tooth row and the other outside it. It is quite simple to rotate the outer side wall 16 around the stud 28, guided by the two limiting walls 30 and 31.

As is made clear from FIG. 7, the contact area between the outer side wall 16 and the base plate 14 includes a trough 32 to engage the outer side wall 16. Within this trough there is a washer device 34 made of silicon, for insulating the outer side wall 16 from the base plate against liquid leakage. Such other insulating materials as rubber or plastic may also be used.

The inner side wall 22 is also engaged in a trough (not shown) in the base plate 14, which trough also has a fluid-insulation device.

Because of the slight separation of the inner or outer side wall 22 or 36 from the base plate 12, 14, it is also possible to combine a series of variously shaped base plates 12, 14 with variously shaped inner or outer side walls 22, 16. In particular, the inner and outer side walls 22, 16 are flexibly formed to enable easy adaptation of the mold tray to the patient's anatomical characteristics. Both side walls of the mold tray shown in FIG. 3 are made of spring-elastic steel.

Figure 8:
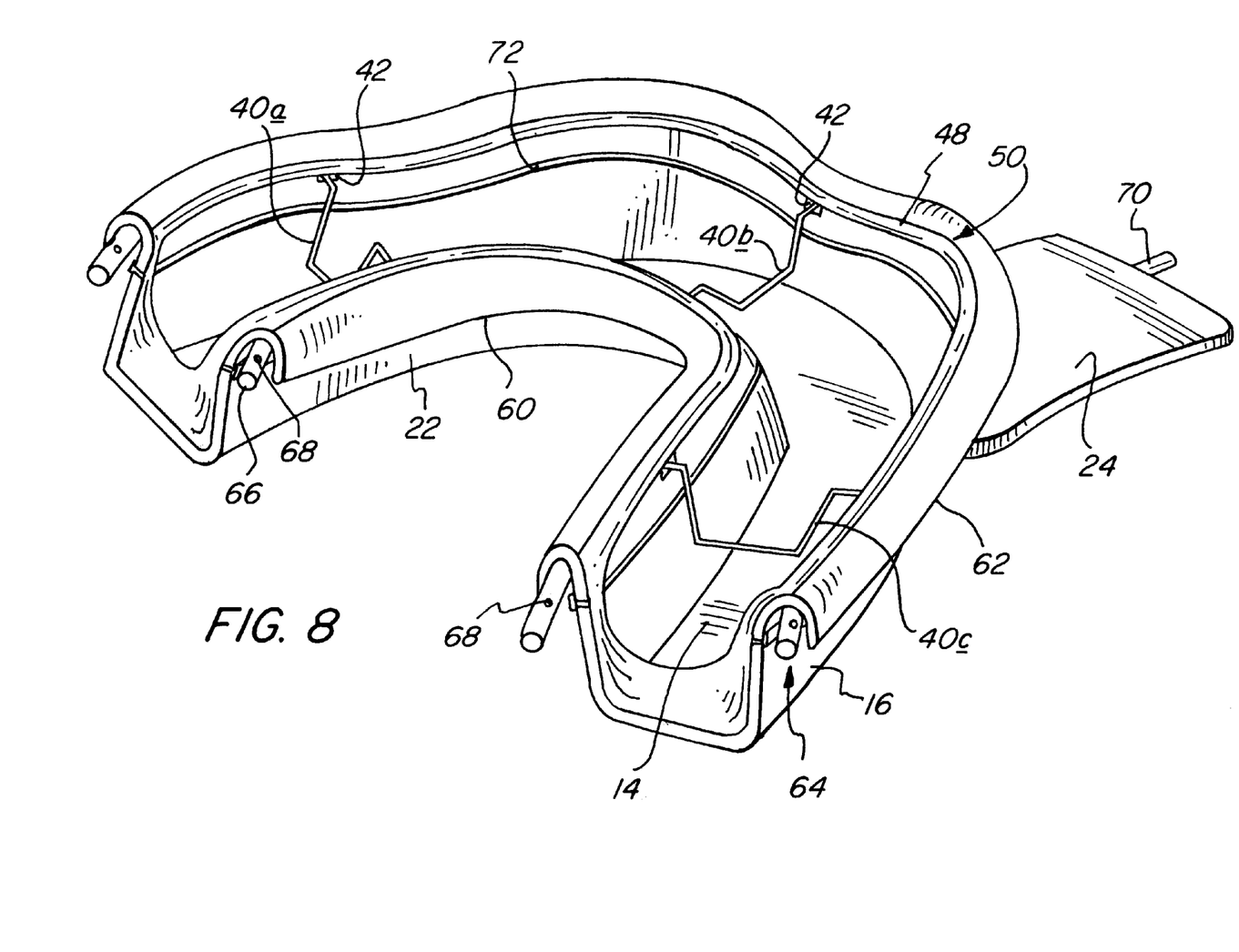
FIG. 8 An additional demonstration of the invention's mold tray for a lower jaw mold in a schematic-perspective view in the molar region.
Figure 9:
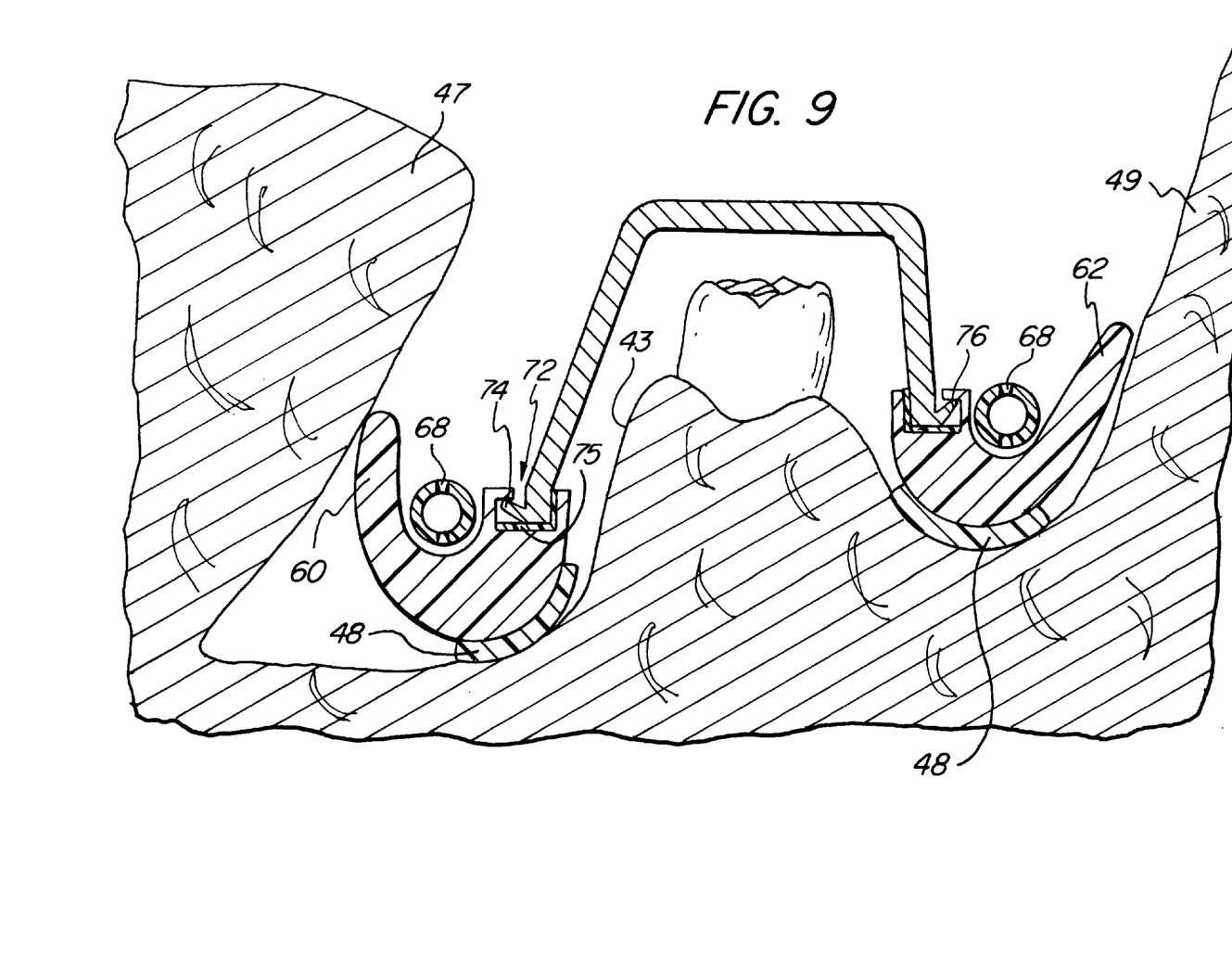
FIG. 9 A schematic partial section of the mold tray according to FIG. 8, with the mold tray in casting position.

FIG. 8 presents yet another mold tray for making casts on the lower jaw, in a cutaway schematic-perspective view in the molar region. FIG. 9 shows a partial cross-sectional view of the same, with the mold tray illustrated in casting position, that is, placed on the tooth row of the lower jaw.

Both the inner and outer side walls 22 and 16 are made of a malleable plastic material. The side walls, likewise, can be made of a spring-elastic steel. With elastic or malleable side walls, to ensure that the mold tray retains the stability required for casting, three studs 40a–40c are placed over the chewing areas between the side walls 22 and 16, with one stud in the incisor area and two in the front molar area. The studs 40a–40c are inserted into corresponding reception units 42 in the side walls 22 and 16, so that the studs 40a–40c are connected with the side walls 22 and 16 securely and tightly against both pushing and pulling. When necessary, that is, for the adaptation of the mold tray to the patient's lower jaw, the studs 40a–40c can be easily removed and reinstalled again after adjustment. When the hardened molding material is being removed, the studs may also be taken out easily.

The mold tray illustrated in FIGS. 8 and 9 includes a molding shell 10, in which the side walls 22 and 16, in their area immediately bordering on the base plate 14, are firmly linked to the base plate. The edge area of the inner and outer side walls 22 and 16 is separable in the edge area turned toward base plate 14. This edge area in the mold tray shown in FIGS. 8 and 9 is formed into a saliva drainage device 64, as described in detail below, with a border that can be individualized.

The saliva drainage device 64 runs, as shown in FIG. 8, along the edge area of the inner and outer side walls 22 and 16 that is turned toward the base plate 14, that is, as shown in FIG. 9, on the mold tray's inside edge area turned toward the tongue 47 and on the outside edge area turned toward the cheek 49 or the lip. The saliva drainage device 64 is made of a plastic material and is elastic and malleable, in order to ensure an exact placement both between the tongue 47 and the membrane 43 on the inside of the tooth row, as well as between the cheek 49 or lip and the membrane outside the tooth row.

Because the inner and outer side walls 22 and 16 are likewise of moldable material, both can be easily adapted to the saliva drainage device 64 and connected to this device. For this purpose the saliva drainage device 64 includes a trough 72 running along its length to both ends in the molar region, for engaging the edge area of the molding shell 10. Inside the trough 72, as FIG. 9 makes clear, an undercutting 74 is formed within the entire trough 72, in which the edge area of the molding shell 10 is engaged by means of a notch projection 76 on the edge area. In this way, a separable yet stable connection is formed between the saliva drainage device 64 and the molding shell 10.

A fluid-proof device 75 is found inside the trough, to prevent any softening of the mold mass or penetration of surrounding air or saliva between the saliva drainage device 64 and the molding shell 10. This insulation device 75 can consist, for instance, of silicon rubber.

Continuing the inner or outer side wall 22 or 16, the saliva drainage device 64 is curved outward from the molding shell in the form of a groove. Within this groove the saliva drainage device 64 includes a saliva drainage channel 66 with a number of drainage openings 68. The saliva drainage device 64 is closed up in the molar region, as indicated in FIG. 8. However, the part of the saliva drainage device 64 turned toward the tongue 47 and the part of the saliva drainage device 64 turned toward the cheek area 49 or the lip can be arranged so as to be separated from one another. The saliva drainage channel 66 is connected by way of a channel (not shown) with a connection 70 for a saliva drainage device (not shown). The connection 70 is placed on the handle, that is, extending out of the mouth. This allows for easy connecting of the saliva drainage pump.

An insulation and balancing element 48 for improved adaptation is included with the saliva drainage device 64 in such a way that the molding shell 10 links up in an insulated form and perfectly fitted on the membrane 43. The insulation and balancing element consists of self-hardening silicon, which when the mold tray is inserted—preferably not filled with molding material, for the sake of appropriate adaptation to the anatomical characteristics of the patient's jaw area—ensures individual adaptation with the maximum insulation.

In FIG. 8 the insulation and balancing element 48 is applied directly to the saliva drainage device 64, inside an engaging device 50 that is shaped roughly like a channel. However, the insulation and balancing element 48 can also be attached directly on the inner and outer side walls 22 and 16, provided that the membrane 43 is connected securely to this. Thus, even without use of the saliva drainage device 64, the insulation and balancing element 48 can be effective.

The mold tray shown in FIG. 9 also has a soft area protection to keep away the tongue and cheek area. As FIG. 9 shows, the groove-shaped saliva drainage device 64, which stands directly against the tongue 47, is equipped with a tongue shield 60, which prevents the tongue 37 from coming in immediate contact with the mold tray 58 and possibly covers up the drainage openings 68 of the saliva drainage channel 66. The area of the saliva drainage device 64, which borders directly on the cheek 49 or the lip, is equipped with a cheek shield 62, which keeps the cheek or the lip well away.

To avoid the necessity for the dentist, in casting the tooth, to be constantly holding or applying the mold tray during the hardening process, the mold tray includes a securing device (not shown) to hold the mold position during the casting process. A chin clamp (not shown) is thus on hand for the lower jaw mold tray illustrated in FIGS. 1, 3, 8, and 9, and a securing strap (which runs across the top of the patient's head) is provided for the upper jaw mold tray shown in FIG. 2.

The mold tray described above, well insulated on the membrane 43, also allows the use of a partial vacuum casting process. For this purpose the mold tray also has a number of drainage openings in the incisor area to produce a vacuum between the membrane or gum 43 and the molding shell 10.

The drainage openings are connected by a drainage channel with a drainage link for a pumping appliance to produce a partial vacuum. The drainage link, for practical reasons, is placed on the handle. In addition, the mold tray includes in the base plate several injection openings in the molar region for the introduction of the mold mass into the molding shell 10. The molding shell 10, as yet unfilled, is "sucked dry" in the casting position or in the gum area 43 by the production of a partial vacuum. With the simultaneous production of the partial vacuum, a liquid molding material is injected through the injection openings, which is self-hardening and, because of its high viscosity, delivers a very exact tooth impression immediately after the injection.

Altogether, with the invention described above it is possible to produce a universal, reusable mold tray which makes possible the production of a very exact dental mold.

What is claimed is:

1. Dental mold tray for producing tooth molds by means of a hardenable mold mass comprising:
   a molding shell conforming to the form of the human jaw for the non-destructive reception of the mold mass and including a base plate and at least one side wall extending from the base plate, said one side wall being removable from the base plate, so that the molding shell is separable into at least two reusable parts; and
   a fluid-proof device between the base plate and the side wall.

2. Mold tray according to claim 1, distinguished in that the molding shell has a base plate adjusted to the gum area and a side wall removably connected to the base plate which surrounds the respective tooth row.

3. Mold tray according to claim 2, distinguished in that the base plate includes a handle extending outward from the tooth row out.

4. Mold tray according to claim 2, distinguished in that the outer side wall is segmented and removable from the base plate.

5. Mold tray according to claim 2, distinguished in that the base plate has a trough for engaging the side wall.

6. Mold tray according to claim 2, distinguished in that the side wall is connected with the base plate by a removable connecting device.

7. Mold tray according to claim 2, distinguished in that the side wall has an extension which, in the connected state of the base plate and the respective side wall, is connected with the handle of the base plate; and the handle and the respective extension are connected with one another by means of a detachable connecting device.

8. Mold tray according to claim 2, distinguished in that the side wall is flexible for adaptation to the base plate.

9. Mold tray according to claim 2, distinguished in that at least one stud for stiffening is included in the molding shell between the base plate and the side wall.

10. Mold tray according to claim 9, distinguished in that at least one stud is secured between the base plate and the side wall, and as necessary can be removed.

11. Mold tray according to claim 9, distinguished in that at least one stud is installed between the base plate and the side wall in corresponding insertion devices so as to be removable.

12. Mold tray according to claim 2, distinguished in that an edge area of the side wall and of the base plate, which comes in contact with the gum during casting includes an elastic element.

13. Mold tray according to claim 12, distinguished in that the elastic element is selected from a group consisting of thermoplast, self-hardening silicon, light-hardening plastic, similar moldable, hardenable material, and combinations of these.

14. Mold tray according to claim 13, distinguished in that the side walls and the base plate include a device for receiving the elastic element.

15. Mold tray according to claim 14, distinguished in that the device for receiving the elastic element has a groove running around the edge area of the side wall and of the base plate.

16. Mold tray according to claim 12, distinguished in that an elastic element is arranged along the saliva drainage device.

17. Mold tray according to claim 16, distinguished in that the saliva drainage device engages the elastic element.

18. Mold tray according to claim 17, distinguished in that the saliva drainage device includes a soft area protection.

19. Mold tray according to claim 2, including at least one drainage opening to produce a partial vacuum.

20. Mold tray according to claim 19, distinguished in that at least one drainage opening is connected with a drainage connection for a pumping device.

21. Mold tray according to claim 20, distinguished in that the drainage connection is located on the handle.

22. Mold tray according to claim 2, including at least one injection opening for introduction of the mold mass into the molding shell.

23. Mold tray according to claim 22, distinguished in that said at least one injection opening is connected with an injection device for the mold mass.

24. Mold tray according to claim 2, including a tongue shield.

25. Mold tray according to claim 2, including a cheek shield.

26. Mold tray according to claim 2, distinguished in that the side wall includes a saliva drainage device for casting on the lower jaw.

27. Mold tray according to claim 26, distinguished in that the saliva drainage device has a saliva drainage channel with a number of drainage openings.

28. Mold tray according to claim 27, distinguished in that the saliva drainage channel has a connection for a saliva drainage pump.

29. Mold tray according to claim 26, distinguished in that the saliva drainage device is detachably connected with the molding shell.

30. Mold tray according to claim 29, distinguished in that the saliva drainage device is connected with the molding shell in a segmented, removable manner.

31. Mold tray according to claim 29, distinguished in that the saliva drainage device is connected with the molding shell by a removable connecting device.

32. Mold tray according to claim 26, distinguished in that the saliva drainage device includes a trough for engaging an edge area of the molding shell.

33. Mold tray according to claim 32, distinguished in that the trough creates a breakable connection between the saliva drainage device and the molding shell.

34. Mold tray according to claim 26, distinguished in that a fluid-proof device is installed between the saliva drainage device and the molding shell.

35. Mold tray according to claim 26, distinguished in that the saliva drainage device is of flexible construction so that it can be adapted to the molding shell and to a patient's jaw.

36. Mold tray according to claim 1, distinguished in that the base plate has a roughly U-shaped tongue opening for upper jaw casting, whose edge is bordered with an inner side wall, which runs at least in part behind the respective tooth.

37. Mold tray according to claim 1, distinguished in that the base plate is vaulted in the direction of the gum for upper jaw casting.

38. Mold tray according to claim 1, distinguished in that the molding shell has a soft covering for the tongue area.

39. Mold tray according to claim 1, distinguished in that the molding shell includes a securing device for holding the molding position during the casting process.

40. Mold tray according to claim 1, distinguished in that the molding shell has a chin clamp for lower jaw casting.

41. Mold tray according to claim 1, distinguished in that for upper jaw casting the mold tray includes a securing strap passing over the patient's head.

42. Dental mold tray for producing tooth molds by means of a hardenable mold mass, comprising:

a molding shell adapted to the shape of the human jaw for receiving the mold mass and having a base plate adapted to the jaw area, and an outer side wall along its edge outside the tooth row, and an inner side wall along its edge inside the tooth row, at least one of said inner and outer walls having an outwardly bent over edge which is spaced from the base plate;

a saliva drainage device received in and extending along the bent over edge, a separable connecting device between one of the side walls and the saliva drainage device, and an elastic element, which during casting produces a fluid-proof contact between the molding shell and the gum.

* * * * *